| United States Patent [19] | [11] Patent Number: 4,657,884 |
| Luft et al. | [45] Date of Patent: Apr. 14, 1987 |

[54] CARRIER-SUPPORTED CATALYST FOR MAKING MONOCARBOXYLIC ANHYDRIDES

[75] Inventors: Gerhard Luft, Mühltal; Gebhard Ritter, Schutterwald, both of Fed. Rep. of Germany

[73] Assignee: Hoechst Aktiengesellschaft, Fed. Rep. of Germany

[21] Appl. No.: 790,726

[22] Filed: Oct. 24, 1985

[30] Foreign Application Priority Data

Nov. 7, 1984 [DE] Fed. Rep. of Germany ....... 3440646

[51] Int. Cl.$^4$ .............................. B01J 31/20
[52] U.S. Cl. ................................... 502/161; 502/153; 502/154; 502/162; 502/167; 502/168; 260/546; 260/549
[58] Field of Search ............... 502/153, 154, 161, 162, 502/167, 168

[56] References Cited

U.S. PATENT DOCUMENTS

| 3,488,296 | 1/1970 | Senn et al. ...................... 502/162 |
| 3,907,852 | 9/1975 | Oswald et al. ................. 502/162 X |
| 4,287,094 | 9/1981 | Panster et al. ................. 502/161 X |

*Primary Examiner*—Patrick P. Garvin
*Attorney, Agent, or Firm*—Connolly and Hutz

[57] ABSTRACT

Carrier-supported catalyst for making monocarboxylic anhydrides by subjecting a suitable ester or ether to carbonylation. The carrier supported catalyst has an organosilicon compound containing an alkoxy or halogen group and also an organonitrogen, organophosphorus, organoarsenic, organosulfur, mercapto or thioether group as a polyfunctional adhesion promoter additively combined with the carrier material on the one hand, and with the noble metal compound of the 8th subgroup of the Periodic System of the elements, on the other hand.

1 Claim, No Drawings

CARRIER-SUPPORTED CATALYST FOR MAKING MONOCARBOXYLIC ANHYDRIDES

This invention relates to a carrier-supported catalyst for making monocarboxylic anhydrides by subjecting a suitable ester or ether to carbonylation, the catalyst having an organosilicon compound containing an alkoxy or halogen group and also an organonitrogen, organophosphorus, organoarsenic, organosulfur, mercapto or thioether group as a polyfunctional adhesion promoter additively combined with the carrier material on the one hand, and with noble metal compound of the 8th subgroup of the Periodic System of the elements, on the other hand.

The preparation of such carrier-supported catalysts and their use for heterogeneous catalysis of olefin hydrogenation reactions and olefin hydroformylation reactions are basically known in the art (cf. K. G. Allum et al., J. Organometallic Chem. 87 (1975), pages 203–216.

The carrier-supported catalyst of this invention is more particularly used for making monocarboxylic anhydrides of the general formula $(RCO)_2O$ by reacting a carboxylic acid ester or dialkylether of the general formulae RCOOR and ROR, respectively, in which R stands for one and the same alkyl group having from 1 to 4 carbon atoms, with carbon monoxide in gas phase in the presence of iodine or bromine or their compounds as a reaction promoter at temperatures of from 130° to 400° C. under pressures of from 1–150 bars.

A process of this kind carried out in gas phase with the use of a carrier-supported catalyst has already been disclosed in German Specification DE-OS No. 24 50 965 and Japanese Specification JP-OS No. 47921/1975, which permits the disadvantages accompanying liquid-phase methods, namely the difficult separation and recycle of suspended and partially dissolved catalyst and optionally promoter, to be avoided.

The gas phase processes described in these two specifications use solid carrier-supported catalysts made by impregnating the carrier with a catalyst solution. In this way, it is not possible, however, e.g. for organonitrogen or organophosphorus compounds containing trivalent nitrogen and phosphorus, respectively, to be fixed in the carrier-supported catalyst, and this has been found generally to affect the activity of the catalyst and selectivity of the reaction.

The present invention also permits the above deficiencies to be obviated, however, by the use of so-called polyfunctional adhesion promoters (spacers) which already have promoters of principal group V, e.g. organylamines or phosphines, integrated therein.

By using them, it is possible realiably to link noble metal compounds of group VIII to the carrier surface area.

Further preferred and optional features of the carrier-supported catalyst of this invention provide:

(a) for it to additionally contain, as a promoter, a compound of a non noble metal belonging to the 1st through 3rd principal group or to the 4th through 6th or 8th subgroups of the Periodic System of the elements;

(b) for the organosilicon compound as the polyfunctional adhesion promoter in the carrier-supported catalyst to be additively combined with the carrier materials on the one hand, and alternately with the noble metal compound and a non noble metal compound selected from the 6th through 8th subgroups of the Periodic System of the elements;

(c) for the polyfunctional adhesion promoter to be an organosilicon compound corresponding to one of the following formulae:

I.  $R_n^1X_{3-n}Si$—$(CR_2^3)_m$—Y or
II. 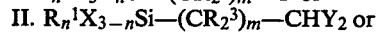 $R_n^1X_{3-n}Si$—$(CR_2^3)_m$—$CHY_2$ or
III.  $[R_n^1X_{3-n}Si$—$(CR_2^3)_m]_2Z$ in which
X stands for —Cl, —Br or —$OR^2$;
Y stands for —$NR_2^4$, a nitrogen-containing aryl group, —$PR_2^4$, —$AsR_2^4$, —$SR^4$ or —SH;
Z stands for —$NR^4$—, $PR^4$—, —$AsR^4$— or —S—;
$R^1$ stands for a $C_1$–$C_5$-alkyl;
$R^2$ stands for a $C_1$–$C_3$-alkyl;
$R^3$ stands for —H, a $C_1$–$C_5$-alkyl or —$C_6H_5$;
$R^4$ stands for a $C_1$–$C_6$-alkyl, a $C_5$–$C_8$-cycloalkyl or —$C_6H_5$ or $C_6H_5CH_2$— which may be substituted with a halogen, methoxy, ethoxy or a $C_1$–$C_3$-alkyl;
n stands for 0 or 1 or 2;
m stands for 0 through 8, preferably 1 through 3;

(d) for it to contain an inorganic oxidic carrier or an active carbon carrier the residual active hydroxy groups of which were inactivated by esterification or etherification;

(e) for it to contain from 0.01 to 50 wgt %, preferably 0.1 to 20 wgt %, noble metal compound, adhesion promoter and non noble metal compound, if desired.

The catalyst carriers should preferably be selected from inorganic oxides, e.g. $SiO_2$, $Al_2O_3$, MgO, $TiO_2$, $La_2O_3$, $ZrO_2$, zeolites, clay, NiO, $Cr_2O_3$, $WO_3$ or corresponding mixed oxides but also active carbon having a BET-surface area of from 1 to 1000 m²/g, preferably 30 to 400 m²/g, and presenting OH-groups. These OH-groups undergo reaction with the functional group or groups of the adhesion promoter with formation of oxygen bridges between carrier and adhesion promoter. The promoters of the 5th or 6th principal group are chemically combined with the adhesion promoter and are themselves one of its functional groups which have the noble metal compounds from group VIII, especially Rh, Ir, Pd or Ru and if desired, non noble metal compounds from the 6th or 8th subgroup, especially Cr or Ni, but also W, Fe, and Co, alternately linked thereto. These noble metal compounds and non noble metal compounds, if any, may well give rise to the formation of bridges between individual adhesion promoter molecules fixed to the carrier.

An advantage of the present invention resides in the fact that the promoters increasing the catalyst activity and selectivity, which are selected from principal group V or VI of the Periodic System of the elements, from a functional group Y or Z in a polyfunctional adhesion promoter and can thus be fixed up to maximum concentration which is determined by the number of OH-groups on the carrier surface. This is the reason why it is not necessary for an organonitrogen or organophosphorus promoter, for example, to be separated and recycled. The process for making monocarboxylic anhydrides catalyzed by the carrier-supported catalyst of this invention compares favorably in catalyst activity and selectivity which are improved with the prior processes referred to hereinabove carried out in gas phase with the use of a carrier-supported catalyst.

The carrier-supported catalyst of this invention is more especially used for making acetic anhydride from methyl acetate or dimethylether in the presence of methyl iodide or methyl bromide as a reaction promoter. HI, HBr or more generally RI or RBr, where R stands for an alkyl group having from 1 to 4 carbon atoms, can also be used as a reaction promoter.

In the general formulae defining the organosilicon compounds which should conveniently be used as adhesion promoters (spacers), X preferably stands for —$OR^2$ and more preferably for methoxy and ethoxy. If n stands for 1 or 2, $R^1$ preferably stands for an unbranched alkyl group, especially methyl, ethyl or propyl.

The useful carrier materials have already been specified hereinabove; useful mixed oxides are e.g. $Cr_2O_3$—$Al_2O_3$, $WO_3$—$Al_2O_3$, $MgO$—$Al_2O_3$, $SiO_2$—$Al_2O_3$ or $ZrO_2$13 $Al_2O_3$. The carrier-supported catalyst preferably contains from 0.01 to 5 wgt % noble metal and is preferably used in form of particles having a size of from 1 to 20 mm.

The noble metal compounds useful for making the carrier-supported catalyst comprise e.g. the following compounds:

Rhodium:
$RhCl_3$, $RhCl_3.3H_2O$, $RhBr_3$, $RhI_3$, $Rh(NO_3)_3$, $Rh_2(CO)_4Cl_2$, $Rh_2(CO)_4Br_2$, $Rh(CO)_4I_2$, $[P(C_6H_5)_3]_3RhCl$, $[P(C_6H_5)_3]_2$, $Rh(CO)Cl$, $RH_6(CO)_{16}$, $RH_4(CO)_{12}$, $Rh_2(O_2CCH_3)_4$, $[RhCl(C_8H_{12})]_2$;

Iridium: $IrCl_3$, $[Ir(CO)_3Cl]_2$, $Ir[P(C_6H_5)_3]_2(CO)Cl$, $Ir_4(CO)_{12}$, $[IrCl(C_8H_{12})]_2$, $Cl(CO)_2Irpyr$ (pyr=$C_6H_5N$);

Palladium:
$PdCl_2$, $PdBr_2$, $PdI_2$, $(CH_3CO_2)_2Pd[P(C_6H_5)_3]_2$, $PdCl_2[P(C_6H_5)_3]_2$, $Pd(O_2CCH_3)_2$, $PdCl_2(C_8H_{12})$, $(C_6H_5CN)_2PdCl_2$;

Ruthenium:
$RuCl_3$, $Ru_3(CO)_{12}$, $RuCl_2[P(C_6H_5)_3]_3$, $RuCl_2(CO)_2[P(C_6H_5)_3]_2$, $[RuCl_2(CO)_3]_2$.

Further useful non noble metal compounds from the 6th or 8th subgroup, especially Cr, Ni, but also W, Fe, Co, which can also be linked to a polyfunctional adhesion promoter, comprise Chromium: $Cr(CO)_6 CrCl_3$, $C_7H_8Cr(CO)_3$
Nickel:
$Ni(CO)HD$ 4, $[P(C_6H_5)_3]_2Ni(CO)_2$, $Ni(C_8H_{12})_2$, $NiCl_2$ The non noble metal compounds from the first to third principal groups or from the the 4th through 6th or 8th subgroups of the Periodic System, preferably of Li, Na, Mg, Ca, Al, Ti, Zr, V, Cr, W, Fe, Co, Ni, should conveniently be selected from hydroxides, carbonates, carbonyls, hydrides, halides and further salts. The non noble metal compounds, e.g. sodium iodide, can be used in form of a solution for impregnating the catalyst carrier therewith.

For preparation of the carrier-supported catalyst of this invention, it is necessary to have the polyfunctional adhesion promoter (organosilicon compound) which is a commercially available product or can be made by methods described in literature. Speaking generally, one of the noble metal compounds of group VIII and, if desired, one of the non noble metal compounds of the 6th or 8th subgroup is additively combined with the adhesion promoter, namely with promoter group Y or Z containing an element selected from the 5th or 6th principal group. Next, the noble metal-containing intermediary product is reactively combined with the hydroxy groups of the carrier material with escape of a group X as a compound XH (e.g. HCl, HBr or $R^2OH$). This is achieved by heating the components suspended in an unpolar solvent (e.g. benzene, toluene, xylene) over a period of 24 to 100 hours until they are found to have been decolorized.

Alternatively, it is also possible first reactively to combine in known manner the polyfunctional adhesion promoter (organosilicon compound) with the hydroxy compounds of the carrier with escape of a group X as a compound XH and only then additively to combine also in known manner, the noble metal compound of group VIII and, if desired, one of the non noble metal compounds of the 6th or 8th subgroup with the promoter group Y or Z of the intermediary product.

Details are indicated in the catalyst description hereinafter.

In order to increase the selectivity and suppress side reactions, it is good practice, especially for discontinuous operation but also for the initial phase in a continuous process, to inactivate those residual OH-groups on the surface of the catalyst carrier which have not reacted with the functional groups X of the adhesion promoter. This can be done e.g. by silylation with trimethylchlorosilane, methylation with methyl iodide or acetylation with acetic anhydride.

The quantitative ratio of carboxylic acid ester or dialkylether and iodine(compound) or bromine(compound) in the reaction zone may vary within wide limits. Generally, however, 1 to 500 mols, preferably 1 to 100 mols, carboxylic acid ester and/or dialkylether is used per 1 mol iodine(compound) or bromine(compound). The temperature selected for the reaction zone should be high enough to always ensure the presence of a gaseous reaction mixture, irrespective of the conversion rate, and preferably is between 170° and 250° C. The preferred pressure is between 10 and 40 bars.

The reaction mixture should conveniently be contacted with solid carrier-supported catalyst over a period of from 1 to 1000 seconds, perferably 1 to 180 seconds. The conversion should suitably be effected in a flow tube arranged in upright position and packed with the carrier-supported catalyst or in an autoclave provided with a stirrer or in a shaking autoclave, having the carrier-supported catalyst placed therein.

The reaction mixture coming from the carbonylation zone is gaseous and contains carbon monoxide, methyl iodide, acetic anhydride, unreacted methyl acetate or dimethylether and, under circumstances, minor proportions of acetic acid. The gaseous reaction mixture is cooled with condensation of acetic anhydride and, under circumstances, acetic acid. Uncondensed gases, such as CO, $CH_3I$, methyl acetate or dimethylether are recycled to the reaction zone, the reacted ester or ether and CO portions being continuously renewed. The anhydrides are easy to separate, i.e. in uncomplicated fashion, by cooling the effluent reaction mixture and recycling the uncondensed gas. This is a particular advantage of the carrier-supported catalyst of this invention. The carrier-supported catalyst is not contaminated; it remains in the reaction zone. As a result, the entire process is rendered considerably simpler.

EXAMPLES

Description relating to catalyst preparation

In order to be activated, the catalyst carriers were in all cases dried for 10 h at 200° C. under a pressure of about 0.133 millibar. All syntheses were effected under nitrogen with exclusion of oxygen and water, and all reagents had previously been dried using molecular screen 4A.

In order to suppress side-reactions and improve the selectivity, the catalysts referred to hereinafter were subsequently treated with trimethylchlorosilane.

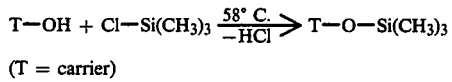

(T = carrier)

To this end, all the catalysts prepared were completely covered with trimethylchlorosilane at room temperature. The respective suspension was heated to boiling and boiled under reflux until gas ceased to be evolved. Next, the suspension was allowed to cool, the catalyst was separated from the liquid and dried at 85° C. over a period of 12 hours under a pressure of 1.33 millibars.

The symbol "$\phi$" used in the formulae hereinafter stands for the phenyl group ($C_6H_5—$).

Autoclave experiments

A stainless steel (Hastelloy C) autoclave (0.25 l capacity) provided with a stirrer, various inlets and outlets and with a turnable basket receiving the catalyst was used. The carboxylic acid esters or dialkylethers were reacted in gas phase with CO-gas in the presence of the massaged or prodded solid carrier-supported catalyst. It was placed in the turnable basket which simultaneously permitted the gases to be thoroughly intermixed. The autoclave was charged with 2.5 ml of a liquid mixture of 20 volume parts methyl iodide and 80 volume parts ester or ether and heated to reaction temperature. The carbonylation was initiated by the injection of carbon monoxide. The CO-pressure was maintained constant by regular replacement of the quantities consumed. Details are indicated in the following Examples.

EXAMPLE 1

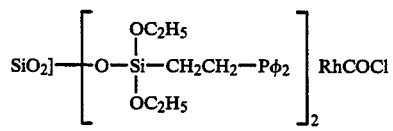

20 g activated silicon dioxide, which had a diameter of 3 mm, an inner BET-surface area of 300 m²/g and a pore volume of 0.95 ml/g, was admixed with 30 ml benzene. Next, the suspension was admixed dropwise while stirring with 3.35 g (37.5 mg Rh) of the compound of the formula [($C_2H_5O$)$_3$SiCH$_2$CH$_2$P$\phi_2$]$_2$RhCOCl (prepared from ($C_2H_5O$)$_3$ SiCH$_2$CH$_2$P$\phi_2$ and [Rh(CO)$_2$Cl]$_2$, cf. K. G. Allum, J. Organo-metallic Chem. 87 (1975), pages 203–216; for preparation of ($C_2H_5O$)$_3$SiCH$_2$CH$_2$P$\phi_2$ from triethoxyvinylsilane and diphenylphosphine with exposure to ultraviolet light, see H. Niebergall, Makromol. Chem. 52 (1962), page 218; for preparation of [Rh(CO)$_2$Cl]$_2$ from RhCl$_3$.3H$_2$O and CO-gas, see J. A. McCleverty et al, Inorg. Synth. 8 (1966, page 211) which was dissolved in benzene, and the whole was heated to boiling. The yellow solution was found to have been completely decolorized after reflux over a period of 24 hours. The benzene solvent was drawn off by suction and the yellowish catalyst was given into a Soxhlet. After 12 h Soxhlet-extraction with benzene as the extractant, the catalyst was dried at 85° C. under 1.33 millibars and thereafter subjected to further treatment with trimethylchlorosilane. The concentrated solutions were free from rhodium. The catalyst so made contained 1.5 wgt % rhodium.

2 ml (1.86 g) methyl acetate, 0.5 ml (1.14 g) methyl iodide and 1.69 g catalyst were reacted in the autoclave with carbon monoxide under a CO-pressure of 20 bars at 200° C. The space/time-yield after a reaction period of 1 h was 4 g Ac$_2$O per gr Rh per hour. The yield of Ac$_2$O, based on the ester, was 4% for a selectivity of 90%.

EXAMPLE 2

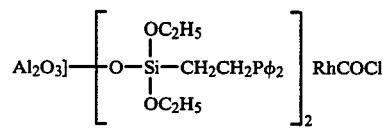

3 g activated aluminum oxide, pellets, which had a diameter of 3 mm, an inner BET-surface area of 125 m²/g and a pore volume of 0.9 ml/g, were added, while stirring, to 200 mg (22.4 mg Rh) of the compound of the formula [($C_2H_5O$)$_3$SiCH$_2$CH$_2$P$\phi_2$]$_2$RhCOCl, which was dissolved in 20 ml xylene. The suspension was heated to boiling. The yellow solution was found to have been completely decolorized after having been refluxed over a period of 48 hours. The xylene solvent was removed by suction and the yellowish catalyst was given into a Soxhlet. After 12 h Soxhlet-extraction with benzene, the catalyst was dried at 85° C. over a period of 8 hours under 1.33 millibars, and then subjected to further treatment with trimethylchlorosilane. The concentrated solutions were free from rhodium. The catalyst so prepared contained 0.7 wgt % rhodium.

2 ml (1.86 g) methyl acetate, 0.5 ml (1.14 g) methyl iodide and 1.58 g catalyst were reacted in the autoclave with carbon monoxide under a CO-pressure of 20 bars at 200° C. The space/time-yield after a reaction period of 1 hour was 80 g Ac$_2$O per g Rh per hour. The yield of Ac$_2$O, based on the ester used, was 34,6% for a selectivity of 96%.

EXAMPLE 3

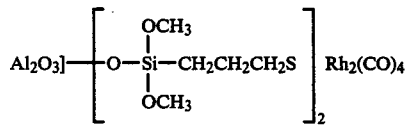

3.2 g dried aluminum oxide pellets, which had a diameter of 3 mm, an inner BET-surface area of 125 m²/g and a pore volume of 0.9 ml were admixed with 3 ml (0.016 mol) of the commercially available compound of the formula (CH$_3$O)$_3$SiCH$_2$CH$_2$CH$_2$SH, which was dissolved in 20 ml toluene, and the whole was heated to boiling. After having been refluxed over a period of 24 hours, the solution was distilled off under reduced pressure and the residue was given into the Soxhlet. After 12 h Soxhlet-extraction with benzene, the pellets were dried overnight at 85° C. and under a pressure of 1 mm of mercury. 3.1 g pellets were admixed at room temperature with 50 mg of the compound of the formula Rh$_2$(CO)$_4$Cl$_2$ in benzene and hydrogen chloride was found to escape at once. After 20 hours, the supernatant solution was found to have been completely decolorized while the pellets were found to have assumed the reedish coloration of the solution. The reddish-brown pellets were filtered off and given into the Soxhlet, extracted for 12 hours with benzene, dried at 85° C. under 1.33 millibars and subjected to further treatment with trimethylchlorosilane. The catalyst so made contained 0.8 wgt % Rh (cf. K. G. Allum et al. J. Organometallic Chem. 87 (1975), pages 203–216).

2 ml (1.86 g) methyl acetate, 0.5 ml (1.14 g) methyl iodide and 1.92 g catalyst were reacted in the autoclave with carbon monoxide under a CO-pressure of 20 bars at 200° C. The space/time-yield after a reaction period of 1 L was 30 g Ac$_2$O per g Rh per hour. The yield of Ac$_2$O, based on the ester used, was 18% for a selectivity of 81%.

EXAMPLE 4

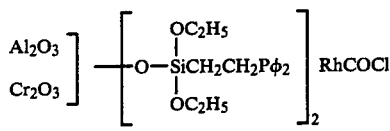

285 mg (31.9 mg Rh) of the compound of the formula [(C$_2$H$_5$O)$_3$SiCH$_2$CH$_2$P$\phi_2$]$_2$RhCOCl, dissolved in 20 ml xylene was added, while stirring, to a mixture of 7 g activated aluminum oxide and 19 wgt % chromium-(III)oxide which had an inner BET-surface area of 60 m$^2$/g and consisted substantially of particles with a size of 2 mm, and the resulting suspension was heated to boiling. After having been refluxed for 48 h, the solution was found to have been completely decolorized. The xylene solvent was distilled off under reduced pressure and the greenish catalyst was given into the Soxhlet. After 12 h Soxhlet-extraction with benzene, the catalyst was dried for 8 h at 85° C. under 1.33 millibars and then subjected to further treatment with trimethylchlorosilane. The concentrated solutions were free from rhodium. The catalyst so made contained 0.4 wgt % rhodium.

2 ml (1.86 g) methyl acetate, 0.5 ml (1.14 g) methyl iodide and 1.95 g catalyst on an Al$_2$O$_3$/Cr$_2$O$_3$-carrier (ratio by weight 5:1) were reacted in the autoclave with carbon monoxide under a CO-pressure of 20 bars at 200° C. The space/time-yield after a reaction period of 1 h was 140 g Ac$_2$O per g Rh per hour. The yield of Ac$_2$O, based on the ester used, was 42.8% for a selectivity of 97.5%.

EXAMPLE 5

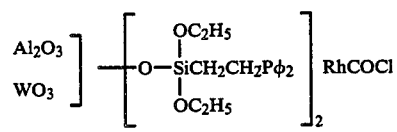

125 mg (14 mg Rh) of the compound of the formula [(C$_2$H$_5$O)$_3$SiCH$_2$CH$_2$P$\phi_2$]$_2$RhCOCl, dissolved in 20 ml xylene, was added, while stirring, to a mixture of 2 g activated aluminum oxide and 10 wgt % tungsten oxide which had an inner BET-surface area of 140 m$^2$/g and consisted substantially of particles with a size of 2 mm, and the suspension was heated to boiling. After having been refluxed over a period of 48 h, the yellow solution was found to have been completely decolorized. The xylene solvent was distilled off under reduced pressure and the catalyst was given into the Soxhlet. After 12 h Soxhlet-extraction with benzene, the catalyst was dried for a period of 8 h at 85° C. under 1.33millibars and then subjected to further treatment with trimethylchlorosilane. The catalyst so made contained 0.66 wgt % rhodium.

2 ml (1.86 g) methyl acetate, 0.5 ml (1.14 g) methyl iodide and 1.9 g catalyst on an Al$_2$O$_3$/WO$_3$-carrier (ratio by weight 10:1) were reacted in the autoclave with carbon monoxide under a CO-pressure of 20 bars at 200° C. The space/time-yield after a reaction period of 1 hour was 90 g Ac$_2$O per gr Rh per hour. The yield of Ac$_2$O, based on the ester used, was 44.2% for a selectivity of 94%.

EXAMPLE 6

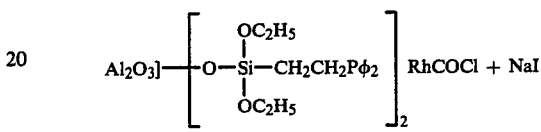

0.1 g sodium iodide, dissolved in 30 ml acetone, was added, while stirring, to 3.1 g activated aluminum oxide (99% Al$_2$O$_3$) which consisted substantially of particles with a size of 3 mm, had an inner BET-surface area of 125 m$^2$/g and a pore volume of 0.9 ml/g, and the whole was heated to boiling. After having been refluxed over a period of 48 hours, the solvent was removed by suction and the catalyst pellets were dried for 4 hours at 85° C. under 1.33 millibars. They contained 2.55 wgt % iodide. The solvent was free from iodide.

3.2 g of this catalyst mass was admixed, while stirring, with 70 mg (7.8 mg Rh) of the compound of the formula [(C$_2$H$_5$O)$_3$SiCH$_2$CH$_P\phi_2$]$_2$RhCOCl which was dissolved in 20 ml xylene, and the suspension was heated to boiling. After having been refluxed for 36 hours, the yellow solution was found to have been completely decolorized. The xylene solvent was removed by suction under reduced pressure and the yellowish catalyst was given into the Soxhlet. After 12 h Soxhlet-extraction with benzene, the catalyst was dried over a period of 8 hours at 85° C. under 1.33 millibars, and then subjected to further treatment with trimethylchlorosilane. The catalyst so made contained 0.24 wgt % rhodium.

2 ml (1.86 g) methyl acetate, 0.5 ml (1.14 g) methyl iodide and 1.66 g catalyst, (ratio by weight Al$_2$O$_3$:-NaI=30:1) were reacted in the autoclave with carbon monoxide under a CO-pressure of 20 bars at 200° C. The space/time-yield after a reaction period of 1 hour was 130 g Ac$_2$O per g Rh per hour. The yield of Ac$_2$O, based on the ester used, was 20.3% for a selectivity of 99%.

EXAMPLE 7

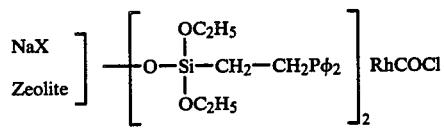

1.07 g (112 mg Rh) of the compound of the formula [(C$_2$H$_5$O)$_3$SiCH$_2$CH$_2$P$\phi_2$]$_2$RhCOCl, dissolved in 100 ml xylene, was added, while stirring, to 25 g activated NaX-zeolite which consisted substantially of particles with a size of 2 mm in diameter and had a BET-surface area of 800 m²/g, and the whole was heated to boiling. After having been refluxed for 72 hours, the solution was found to have been completely decolorized. The solvent was removed by suction and the catalyst was given into the Soxhlet. After 12 h Soxhlet-extraction with benzene, the catalyst was dried over a period of 8 hours at 85° C. under 1.33 millibars, and then subjected to further treatment with trimethylchlorosilane. The catalyst so made contained 0.26 wgt % rhodium.

2 ml (1.86 g) methyl acetate, 0.5 ml (1.14 g) methyl iodide and 2.65 g catalyst were reacted in the autoclave with carbon monoxide under a CO-pressure of 20 bars at 200° C. The space/time-yield after a reaction period of 1 hour was 70 g Ac₂O per g Rh per hour. The yield of Ac₂O, based on the ester used, was 14.5% for a selectivity of 88%.

EXAMPLE 8

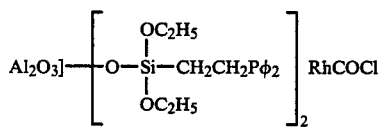

The catalyst was made as described in Example 2 but it contained 0.6 wgt % rhodium.

A steel tube 20 mm wide and 450 mm long was arranged in upright position and used as a flow tube which was filled with 35 g catalyst, 30 Nl CO (Nl=liter measured at 1.013 bar and 0° C.) per hour and an evaporated mixture (10 ml liquid of methyl acetate and methyl iodide (molar ratio 11:1) was passed through the flow tube under a pressure of 10 bars at 180° C.

The effluent reaction mixture was cooled to 0° C. at atmospheric pressure and analyzed gas-chromatographically. A space/time-yield of 11.2 g Ac₂O per g Rh per hour was obtained. The yield of Ac₂O, based on the ester used, was 18.7% for a selectivity of 98%.

The carbonylation was effected over a period of 200 hours under these conditions after which the performance of the carrier-supported catalyst could not be found to have been impaired.

EXAMPLE 9

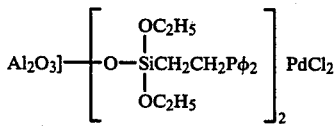

140 mg (15.8 mg Pd) of the compound of the formula [(C₂H₅O)₃SiCH₂CH₂Pφ₂]₂PdCl₂ (prepared from (C₂H₅O)₃SiCH₂CH₂Pφ₂ and Pd(CH₃CO₂)₂ or (C₆H₅CN)₂PdCl₂ or PdCl₂(C₈H₁₂), cf. K. Kochloefl et al J. Chem. Soc. (London) Chem. Com 1977, pages 510–511 and L. Bemi et al JACS 104 (1982) pages 438–445), which was dissolved in a mixture of 10 ml benzene and 10 ml dichloromethane, was added while stirring to 3.1 g activated aluminum oxide (99% Al₂O₃) which consisted substantially of particles with a size 3 mm in diameter, had an inner BET-surface area of 125 m²/g and a pore volume of 0.9 ml/g, and the suspension was heated to boiling. After having been refluxed over a period of 56 hours, the yellow solution was found to have been completely decolorized. The solvent mixture was removed by suction and the yellowish catalyst was given into the Soxhlet. After 12 h Soxhlet-extraction with benzene, the catalyst was dried for 8 hours at 85° C. under 1.33 millibars and then subjected to further treatment with trimethylchlorosilane. The concentrated solutions were free from palladium. The catalyst so made contained 0.37 wgt % palladium.

2 ml (1.86 g) methyl acetate, 0.5 ml (1.14 g) methyl iodide and 1.93 g catalyst were reacted in the autoclave with carbon monoxide under a CO-pressure of bars at 200° C. The space/time-yield after a reaction period of 1 h was 20 g Ac₂O per g Pd per hour. The yield of Ac₂O, based on the ester used, was 5.6% for a selectivity of 99.5%.

EXAMPLE 10

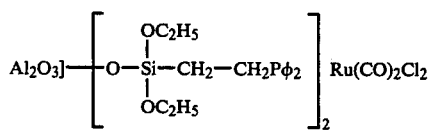

140 mg (15.5 mg Ru) of the compound of the formula [(C₂H₅O)₃SiCH₂CH₂Pφ₂]₂Ru(CO)₂Cl₂ (prepared from (C₂H₅O)₃SiCH₂CH₂Pφ₂ and (Pφ₃)₂RuCl₂(CO)₂, cf. Pittman Jr. et al JACS (1975), page 1749) which was dissolved in a mixture of 15 ml dichloromethane and 15 ml benzene was added, while stirring, to 3.2 g activated aluminum oxide (99% Al₂O₃) which consisted substantially of particles with a size of 3 mm in diameter, had an inner BET-surface area of 125 m²/g and a pore volume of 0.9 ml/g, and the suspension was heated to boiling. After having been refluxed for 72 hours, the solution was found to have been decolorized. After separation of the solvent mixture, the catalyst was given into the Soxhlet. After 12 h Soxhlet-extraction with benzene, the catalyst was dried for 8 hours at 85° C. under 1.33 millibars and then subjected to further treatment with trimethylchlorosilane. The concentrated solutions were free from ruthenium. The catalyst so made contained 0.48 wgt % ruthenium.

2 ml (1.86 g) methyl acetate, 0.5 ml (1.14 g) methyl iodide and 1.92 g catalyst were reacted in the autoclave with carbon monoxide under a CO-pressure of 20 bars at 200° C. The space/time-yield after a reaction period of 1 hour was 10 g Ac₂O per g Ru per hour. The yield of Ac₂O, based on the ester used, was 3.61% for a selectivity of 99.5%.

EXAMPLE 11

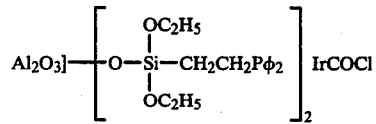

125 mg (23.8 mg Ir) of the compound of the formula [(C₂H₅O)₃SiCH₂CH₂Pφ₂]₂IrCOCl (prepared from (C₂H₅O)₃SiCH₂CH₂Pφ₂ and [IrCl(C₈H₁₂)]₂ or Cl(CO)₂Irpyr or IrClCO(Pφ₃)₂, cf. C. U. Pittman Jr. et al., JACS 97 (inner 1975), pages 4774–4775) which was dissolved in 100 ml toluene was added to 5.6 g activated aluminum oxide (99% Al₂O₃) which consisted substantially of particles with a diameter of 3 mm, had an inner BET-surface area of 125 m²/g and a pore volume of 0.9 ml/g, and the whole was heated to boiling. After having been refluxed for 100 hours the solution was found to have been completely decolorized. After separation of the solvent, the catalyst was given into the Soxhlet. After 12 h Soxhlet-extraction with benzene, the catalyst was dried for 8 hours at 85° C. under 1.33 millibars. The concentrated solutions were free from iridium. The catalyst so made contained 0.41 wgt % iridium.

2 ml (1.86 g) methyl acetate, 0.5 ml (1.14 g) methyl iodide and 3.5 g catalyst were reacted in the autoclave with carbon monoxide under a CO-pressure of 20 bars at 200° C. The space/time-yield after a reaction period of 1 hour was 20 g $Ac_2O$ per g Ir per hour. The yield of $Ac_2O$, based on the ester used, was 11.4% for a selectivity of 97.5%.

EXAMPLE 12

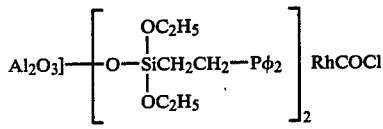

The catalyst was made as described in Example 2, but it contained 0.9 wgt % rhodium.

1.86 g dimethylether, 0.5 ml (1.14 g) methyl iodide and 1.92 g catalyst were reacted in the autoclave with carbon monoxide under a CO-pressure of 20 bars at 200° C. The space/time-yield was 30 g $Ac_2O$ per g Rh per hour. The yield of $Ac_2O$ after 2 hours, based on the ether used, was 12.7% for a selectivity of 66%.

The principal by-product was methyl acetate.

EXAMPLE 13

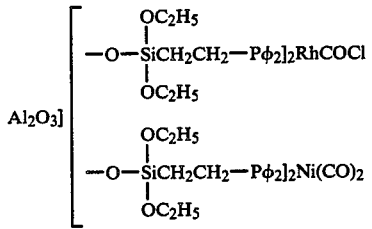

100 mg (11.2 mg Rh) of the compound of the formula [($C_2H_5O$)$_3SiCH_2CH_2P\phi_2$]$_2$RhCOCl and 100 mg (6.7 mg Ni) of the compound of the formula [($C_2H_5O$)$_3$-$SiCH_2CH_2P\phi_2$]$_2$Ni(CO)$_2$ (prepared from ($C_2H_5O$)$_3$-$SiCH_2CH_2P\phi_2$ and [Rh(CO)$_2$Cl]$_2$, and Ni(CO)$_4$, cf. A. K. Smith et al. J. mol. Catal. 2 (1977), pages 223–226) which were dissolved in 40 ml xylene, were added, while stirring, to 3.2 g activated aluminum oxide (99% $Al_2O_3$) which consisted substantially of particles 3 mm in diameter, had an inner BET-surface area of 125 m$^2$/g and a pore volume of 0.9 ml/g, and the suspension was heated to boiling. After having been refluxed over a period of 72 hours, the yellow solution was found to have been decolorized. After separation of the solvent, the catalyst was given into the Soxhlet. After 12 h Soxhlet-extraction with benzene, the catalyst was dried for 8 hours at 95° C. under 1.33 millibars and subjected to further treatment with trimethylchlorosilane. The concentrated solutions were free from rhodium and nickel. The catalyst so made contained 0.33 wgt % rhodium and 0.19 wgt % nickel promoter.

2 ml (1.86 g) methyl acetate, 0.5 ml (1.14 g) methyl iodide and 1.6 g catalyst were reacted in the autoclave with carbon monoxide under a CO-pressure of 20 bars at 200° C. The space/time-yield after a reaction period of 1 h was 110 g $Ac_2O$ per g Rh per hour. The yield of $Ac_2O$, based on the ester used, was 38% for a selectivity of 93%.

EXAMPLE 14

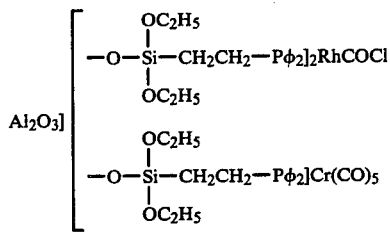

100 mg (11.2 mg Rh) of the compound of the formula [($C_2H_5O$)$_3SiCH_2CH_2P\phi_2$]$_2$RhCOCl and 125 mg (11.4 mg Cr) of the compound of the formula [($C_2H_5O$)$_3$-$SiCH_2CH_2P\phi_2$]Cr(CO)$_5$ (prepared from ($C_2H_5O$)$_3$-$SiCH_2CH_2P\phi_2$ and [Rh(CO)$_2$Cl]$_2$, and Cr(CO)$_6$, respectively, cf. C. N. Matthews et al JACS 81 (1959), pages 2273–2274) which were dissolved in 40 ml xylene, were added, while stirring to 3.2 g activated aluminum oxide (99% $Al_2O_3$) which consisted substantially of particles 3 mm in diameter, had an inner BET-surface area of 125 m$^2$/g and a pore volume of 0.9 ml/g, and the suspension was heated to boiling. After having been refluxed for 72 hours, the yellow solution was found to have been completely decolorized. The solvent was separated and the catalyst was given into the Soxhlet. After 12 h Soxhlet-extraction with benzene, the catalyst was dried for 8 hours at 85° C. under 1.33 millibars and then subjected to further treatment with trimethylchlorosilane. The concentrated solvents were free from rhodium and nickel. The catalyst so made contained 0.33 wgt % rhodium and 0.3 wgt % chromium promoter.

2 ml (1.86 g) methyl acetate, 0.5 ml (1.14 g) methyl iodide and 1.6 g catalyst were reacted in the autoclave with carbon monoxide under a CO-pressure of 20 bars at 200° C. The space/time-yield after a reaction period of 1 h was 120 g $Ac_2O$ per g Rh per hour. The yield of $Ac_2O$, based on the ester used, was 38% for a selectivity of 96%.

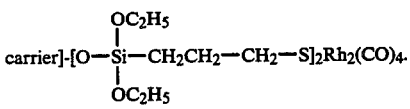

We claim:
1. A carrier-supported catalyst for making monocarboxylic anhydrides by carbonylation of a suitable ester or ether, the carrier-supported catalyst corresponding to the formula